United States Patent
Enderlein

(10) Patent No.: US 9,111,366 B2
(45) Date of Patent: *Aug. 18, 2015

(54) SUPERRESOLUTION OPTICAL FLUCTUATION IMAGING (SOFI)

(71) Applicant: SOFast GmbH, Berlin (DE)

(72) Inventor: Joerg Enderlein, Berlin (DE)

(73) Assignee: Sofast GmbH, Berlin (DE)

( * ) Notice: Subject to any disclaimer, the term of this patent is extended or adjusted under 35 U.S.C. 154(b) by 155 days.

This patent is subject to a terminal disclaimer.

(21) Appl. No.: 14/021,553

(22) Filed: Sep. 9, 2013

(65) Prior Publication Data

US 2014/0099043 A1 Apr. 10, 2014

Related U.S. Application Data

(63) Continuation of application No. 12/791,997, filed on Jun. 2, 2010, now Pat. No. 8,625,863.

(60) Provisional application No. 61/183,519, filed on Jun. 2, 2009.

(51) Int. Cl.
| | |
|---|---|
| *G06T 3/40* | (2006.01) |
| *H04N 5/232* | (2006.01) |
| *G01N 21/64* | (2006.01) |
| *G02B 21/00* | (2006.01) |

(Continued)

(52) U.S. Cl.
CPC ............ *G06T 3/4053* (2013.01); *G02B 21/367* (2013.01); *G02B 27/58* (2013.01); *H04N 5/23232* (2013.01); *G01N 21/6458* (2013.01); *G02B 21/008* (2013.01); *G02B 21/0076* (2013.01); *G06T 2207/10056* (2013.01); *G06T 2207/10064* (2013.01)

(58) Field of Classification Search
None
See application file for complete search history.

(56) References Cited

U.S. PATENT DOCUMENTS

| | | | |
|---|---|---|---|
| 5,671,085 A | 9/1997 | Gustafsson et al. | |
| 5,731,588 A | 3/1998 | Hell et al. | |

(Continued)

FOREIGN PATENT DOCUMENTS

| | | | |
|---|---|---|---|
| JP | 2003531371 A | 10/2003 | |
| JP | 2004108892 A | 4/2004 | |
| WO | 2004072624 A1 | 8/2004 | |

OTHER PUBLICATIONS

Huang, Bo, Mark Bates, and Xiaowei Zhuang. "Super resolution fluorescence microscopy." Annual review of biochemistry 78 (Mar. 2009).*

(Continued)

*Primary Examiner* — Kim Vu
*Assistant Examiner* — Nathan Bloom
(74) *Attorney, Agent, or Firm* — Laurence A. Greenberg; Werner H. Stemer; Ralph E. Locher

(57) ABSTRACT

Statistical analysis techniques based on auto- and cross-correlations/cumulants, of image stacks of fluctuating objects are used to improve resolution beyond the classical diffraction limit and to reduce the background. The time trajectory of every pixel in the image frame is correlated with itself and/or with the time trajectory of an adjacent pixel. The amplitude of these auto- or cross-correlations/cumulants of each pixel, at a given time lag or averaged or integrated over an interval of time lags, is used as the intensity value of that pixel in the generated superresolved optical fluctuation image.

15 Claims, 25 Drawing Sheets

(51) Int. Cl.
G02B 21/36 (2006.01)
G02B 27/58 (2006.01)

(56) References Cited

U.S. PATENT DOCUMENTS

| | | | |
|---|---|---|---|
| 6,813,569 | B2 | 11/2004 | Wohland et al. |
| 7,064,824 | B2 | 6/2006 | Hell |
| 7,253,893 | B2 | 8/2007 | Hell et al. |
| 7,373,019 | B2 | 5/2008 | Zomet et al. |
| 7,400,396 | B2 | 7/2008 | Watanabe et al. |
| 7,430,045 | B2 | 9/2008 | Hell |
| 7,535,012 | B2 | 5/2009 | Betzig et al. |
| 7,538,893 | B2 | 5/2009 | Hell et al. |
| 7,626,694 | B2 | 12/2009 | Betzig et al. |
| 7,626,695 | B2 | 12/2009 | Betzig et al. |
| 7,626,703 | B2 | 12/2009 | Betzig et al. |
| 7,710,563 | B2 | 5/2010 | Betzig et al. |
| 7,719,679 | B2 | 5/2010 | Hell et al. |
| 2006/0159369 | A1 | 7/2006 | Young |
| 2009/0037134 | A1* | 2/2009 | Kulkarni et al. ............ 702/127 |
| 2009/0041320 | A1 | 2/2009 | Tanaka |
| 2009/0154816 | A1 | 6/2009 | Swazey et al. |
| 2009/0194702 | A1* | 8/2009 | Meyers et al. ............... 250/393 |
| 2009/0237501 | A1 | 9/2009 | Lemmer et al. |
| 2010/0207037 | A1* | 8/2010 | Tearney et al. ........... 250/459.1 |
| 2012/0190098 | A1 | 7/2012 | Twieg et al. |
| 2014/0353475 | A1* | 12/2014 | Meyers et al. ............... 250/216 |

OTHER PUBLICATIONS

Vukojevi, V., et al. "Study of molecular events in cells by fluorescence correlation spectroscopy." Cellular and molecular life sciences 62.5 (2005): 535-550.

Elke Haustein & Petra Schwille (2007): Trends in fluorescence imaging and related techniques to unravel biological information, HFSP Journal, 1:3, 169-180.

Artem V. Melnykov and Kathleen B. Hall, Revival of High-Order Fluorescence Correlation Analysis: Generalized Theory and Biochemical Applications, The Journal of Physical Chemistry, Oct. 2009 113 (47), 15629-15638.

E. M. Ismaili Aalaoui, E. Ibn-Elhaj, and E. H. Bouyakhf. 2009. A robust subpixel motion estimation algorithm using HOS in the parametric domain. J. Image Video Process. 2009, Article 2 (Jan. 2009).

B Christoffer Lagerholm, Laurel Averett, Gabriel E. Weinreb, Ken Jacobson, Nancy L. Thompson, Analysis Method for Measuring Submicroscopic Distances with Blinking Quantum Dots, Biophysical Journal, vol. 91, Issue 8, Oct. 15, 2006, pp. 3050-3060, ISSN 0006-3495.

Ventalon et al., "Dynamic Speckle Illumination Microscopy with Wavelet Prefiltering," Optics Letters, vol. 32, No. 11, Jun. 1, 2007, pp. 1417-1419.

Betzig et al., "Imaging Intracellular Fluorescent Proteins at Nanometer Resolution," Science, vol. 313, Sep. 15, 2006, pp. 1642-1645.

Gustafsson, M. G. L., "Surpassing the Lateral Resolution Limit by a Factor of Two Using Structured Illumination Microscopy," Journal of Microscopy, vol. 198, Pt. 2, May 2000, pp. 62-67.

Gustafsson et al., "I.sup.5M: 3D Widefield Light Microscopy with Better Than 100nm Axial Resolution," The Royal Microscopical Society, Journal of Microscopy, vol. 195, 1999, pp. 10-16.

Heintzmann et al., "Saturated Patterned Excitation Microscopy—A Concept for Optical Resolution Improvement," J. Opt. Soc. Am. A. vol. 19, No. 6, Aug. 2002, pp. 1599-1609.

Hell et al., "Ground-State-Depletion Fluorescence Microscopy: A Concept for Breaking the Diffraction Resolution Limit," Appl. Phys. B, vol. 60, 1995, pp. 495-497.

Hell et al., "Breaking the Diffraction Resolution Limit by Stimulated Emission: Stimulated-Emission-Depletion Fluorescence Microscopy," Optics Letters, vol. 19, No. 11, Jun. 1, 1994, pp. 780-782.

Hess et al., "Ultra-High Resolution Imaging by Fluorescence Photoactivation Localization Microscopy," Biophysical Journal, vol. 91, Dec. 2006, pp. 4258-4272.

Huang et al., "Whole Cell 3D STORM Reveals Interactions Between Cellular Structures with Nanometer-Scale Resolution," NIH-PA Author Manuscript. Published in final edited form as: Nat. Methods, vol. 5, No. 12, Dec. 2008, pp. 1047-1052.

Juette et al., "Three-Dimensional Sub-100 nm Resolution Fluorescence Microscopy of Thick Samples," Nature Methods, vol. 5, No. 6, Jun. 2006, pp. 527-529.

Klar et al., "Subdiffraction Resolution in Far-Field Fluorescence Microscopy," Optics Letters, vol. 24, No. 14, Jul. 15, 1999, pp. 954-956.

Lidke et al., "Superresolution by Localization of Quantum Dots Using Blinking Statistics," Optics Express, vol. 13, No. 18, Sep. 5, 2005, pp. 7052-7062.

Marriott et al., "Optical Lock-in Detection Imaging Microscopy for Contrast-Enhanced Imaging in Living Cells," Proc. Natl. Acad. Sci., vol. 105, No. 46, Nov. 18, 2006, pp. 17789-17794.

Mendel, J. M., "Tutorial on Higher-Order Statistics (Spectra) in Signal Processing and System Theory: Theoretical Results and Some Applications," Proc. IEEE, vol. 79, No. 3, Mar. 1991, pp. 278-305.

Rust et al., "Stochastic Optical Reconstruction Microscopy (STORM) Provides Sub-Diffraction-Limit Image Resolution," NIH PA Author Manuscript. Published in final edited form as Nat. Methods, vol. 3, No. 10, Oct. 2006, pp. 793-795.

Shtengel et al., "Interferometric Fluorescent Super-Resolution Microscopy Resolves 3D Cellular Ultrastructure," Proc. Natl. Acad. Sci., vol. 106, No. 9, Mar. 3, 2009, pp. 3125-3130.

* cited by examiner

Schematic of second-order SOFI image generation

Schematic of second-order SOFI image generation

Schematic of second-order SOFI image generation

Schematic of second-order SOFI image generation

Schematic of second-order SOFI image generation

Schematic of second-order SOFI image generation

Generation of a second-order SOFI image based on auto-correlations

1) Providing a sample comprised of point-source like- emitters (as compared to the extent of the imaging system's PSF).

⇩

2) Emitters exhibit some optical measurable fluctuation (blinking), which either occur intrinsically or can be induced externally (e.g. by light, chemicals etc.). Emitters fluctuate stochastically and independently of each other.

⇩

3) Providing an optical imaging system, excitation light(s), and detector(s) capable of recording the fluctuations in images as function of time (movie, or image stack).

⇩

4) The microscope magnification is adjusted to oversample the PSF (~4x4 pixels per PSF).

⇩

5) The imaging system records the spatio-temporal signals from the emitters in an image stack (movie)

⇩

6) After recording, a time trajectory is extracted for each pixel

⇩

7) The mean value is substracted from each time trajectory

⇩

8) The second-order temporal auto-correlation function of the zero-mean time trajectory is calculated for each pixel

⇩

9) The first non-zero time lag combination (i.e. $\tau_1 = 0, \tau_2 = 1$) of the auto-correlation function is assigned as the intensity of the corresponding SOFI pixel. Time lags are in units of frames of the movie.

⇩

10) The generated image from these pixels is the second-order SOFI image

FIG. 2

Obtaining a SOFI image based on the second-order auto-correlation function using different time lag configurations

Obtaining a SOFI image based on the second-order auto-correlation function using different time lag configurations

Obtaining a SOFI image based on the second-order auto-correlation function using different time lag configurations

Obtaining a SOFI image based on the second-order cross-correlation function using different time lag configurations Obtaining a SOFI image based on the second-order cross-correlation function using different time lag configurations Obtaining a SOFI image based on the second-order cross-correlation function
using different time lag configurations Interleaved pixels and their weighting for the second-order SOFI images based on cross-correlations Interleaved pixels and their weighting for the second-order SOFI images based on cross-correlations Interleaved pixels and their weighting for the second-order SOFI images based on cross-correlations

Generate interleaving pixels using cross-cumulants and correcting for the distance factor 1) A movie is recorded as schematically shown in Fig. 1 and described in the flowchart of Fig. 2.

2) Additionally to the second-order auto-correlations, the pixel time trajectories of directly adjacent pixels (e.g. $r_1, r_2$) are used for calculating the second-order cross-correlations (see Fig. 5).

3) According to Eq. (11), the location of the resulting pixel $r$ is given by the geometric center of both pixels $r_1, r_2$ and is called interleaving pixel

4) $r$ is derived from the cross-correlations using the exact same time lag combination $\tau_1, \tau_2$ as used for the generation of the SOFI pixels at $r_1$ and $r_2$ using auto-correlations.

5) The intensities of all pixels $r_1, r_2, r$ are divided by their corresponding distance factors. In this example $r_1$ and $r_2$ are obtained using auto-correlations. In this case the distance factor equals 1. (Eq. (23)). This can also be seen from Fig. 5(b). and 5(c). The distance factor is calculated based on the pixels' time trajectories used to generate the respective SOFI pixel.

FIG.6

Possible second-order cross-correlations to obtain a fully up-sampled SOFI image Possible second-order cross-correlations to obtain a fully up-sampled SOFI image Possible second-order cross-correlations to obtain a fully up-sampled SOFI image Possible second-order cross-correlations to obtain a fully up-sampled SOFI image

Flowchart to generate an up-sampled second-order SOFI image using second-order auto- and cross-correlations.

Calculating the same SOFI pixel using different pixel time trajectories

Calculating the same SOFI pixel using different pixel time trajectories

SUPERRESOLUTION OPTICAL FLUCTUATION IMAGING (SOFI)

REFERENCE TO RELATED APPLICATIONS

This application relies for priority on provisional application No. 61/183,519 of Jörg Enderlein, filed on Jun. 2, 2009 and entitled "Superresolution optical fluctuation imaging (SOFI)"

FIELD OF THE INVENTION

This invention relates generally to sub-diffraction and background reduction optical (or electromagnetic) imaging methods based on a signal processing method of data stacks (sequence of multiple x-y images/frames as function of time i.e. a movie). The method relies on multiple-order auto- and cross-correlation (and auto/cross cumulants) statistical analysis of temporal fluctuations (caused, for example, by fluorescence blinking/intermittency) recorded in a sequence of images (a movie). The method can be applied to superresolve stationary and non-stationary samples composed of light-emitting, absorbing or scattering blinking objects. Fields of use include microscopy, telescopy, medical imaging, and other forms of electromagnetic imaging.

DESCRIPTION OF RELATED ART

The publications, patents, and other reference materials referred to herein describe the background of the invention and to provide additional detail regarding its practice are hereby incorporated.

Spatial resolution of optical imaging methods (microscopies, telescopies etc.) are limited by the diffraction limit of light (Abbe's limit). Optical microscopies, and in particular fluorescence microscopy, permit three-dimensional (3D) investigation of living cells, tissues and live organisms. However, features smaller than approximately half the emission wavelength (~200-300 nm) for visible light cannot be resolved in conventional far-field microscopy due to the above mentioned limit. Similarly, astronomical observations cannot resolve neighboring celestial objects below the diffraction limit of light.

Other non-optical imaging techniques, such as electron microscopy (scanning electron microscope, transmission electron microscope, cryo-electron microscope) and scanning probe microscopy (scanning tunneling microscope, atomic force microscope), achieve molecular-level resolution, but are not suitable for imaging features within live cells. They are limited to analyzing surfaces (membranes) or to fixed and thinly sectioned samples.

During the last decade, the optical diffraction limit has been overcome with the introduction of several new concepts, as discussed below.

Hell and Wichmann, "Breaking the diffraction resolution limit by stimulated emission: Stimulated-emission-depletion fluorescence microscopy", 1994, Optical Society of America, Optics Letters, vol. 19, pp. 780-782, Hell and Kroug, "Ground-state-depletion fluorescence microscopy: A concept for breaking the diffraction resolution limit", 1995, Applied Physics B, Lasers Optics, vol. 60, pp. 495-497, Klar et al. "Subdiffraction resolution in far-field fluorescence microscopy", Jul. 15, 1999, Optical Society of America, Optics Letters, vol. 24, No. 14, pp. 954-956, U.S. Pat. Nos. 5,731,588, 7,719,679, 7,538,893, 7,430,045, 7,253,893, and 7,064,824 teach stimulated emission depletion (STED) microscopy and related methods, requiring special apparatuses, special emitters (fluorophores) and relatively strong laser illumination.

Gustafsson, "Surpassing the lateral resolution limit by a factor of two using structured illumination microscopy", 2000, Journal of Microscopy, vol. 198, pp. 82-87, Heintzmann et al., "Saturated patterned excitation microscopy: A concept for optical resolution improvement", 2002, Journal of Optical Society of America A, vol. 19, pp. 1599-1609, Gustafsson et al., (IM)-M-5: "3D wide-field light microscopy with better than 100-nm axial resolution", 1999, Journal of Microscopy, vol. 195, pp. 10-16, and U.S. Pat. No. 5,671,085 teach structured illumination microscopy and saturated structured illumination microscopy (SIM/SSIM) and image interference microscopy ($I^5M$).

Betzig et al. "Imaging intracellular fluorescent proteins at nanometer resolution", 2006, Science, vol. 313, pp., 1642-1645, Hess et al. "Ultra-high-resolution imaging by fluorescence photoactivation localization microscopy", 2006, Biophysics Journal, vol. 91, pp. 4258-4272, U.S. Pat. Nos. 7,710,563, 7,626,703, 7,626,695, 7,626,694, 7,535,012 teach photo-activated localization microscopy (PALM) and related methods; Rust et al., "Subdiffraction-limit imaging by stochastic optical reconstruction microscopy (STORM)", 2006, Nature Methods, vol. 3, pp. 793-795 teach the related stochastic optical reconstruction microscopy (STORM) method.

The development of switchable fluorescent probes also triggered the emergence of new background-reducing, contrast-enhancing techniques such as optical lock-in detection (OLID) as taught by Marriott et al., "Optical lock-in detection imaging microscopy for contrast enhanced imaging in living cells", 2008, Proceedings of the National Academy of Science, USA, vol. 105, pp. 17789-17794.

STED has achieved video-rate resolution enhancement but the method is quite demanding in terms of the labeling procedures, choice of dyes, and requires tedious alignment procedures, which are challenging. Recently superresolution microscopy at 11 Hz has been demonstrated using SIM, achieving a twofold increased lateral resolution. All superresolution methods are capable of enhancing the resolution in 3D, but often at the expense of major technical demands or modifications to the microscope, as taught in Shtengel et al., "Interferometric fluorescent super-resolution microscopy resolves 3D cellular ultrastructure", 2009, Proceedings of the National Academy of Science, USA, vol. 106, pp. 3125-3130, Juette et al., "Three-dimensional sub-100-nm resolution fluorescence microscopy of thick samples", 2008, Nature Methods, vol. 5, pp. 527-529, Huang et al., "Whole-cell 3D STORM reveals interactions between cellular structures with nanometer-scale resolution", 2008, Nature Methods, vol. 5, pp. 1047-1052. PALM and STORM achieve nanometer resolution, but with the trade-off of slow acquisition speed. The acquisition of a full superresolution image usually takes minutes to hours. Lastly, even though OLID provides fast imaging with enhanced contrast, it lacks superresolution capability.

Lidke et al. teach in "Superresolution by localization of quantum dots using blinking statistics", 2005, Opics Express vol. 13, pp. 7052-7062 an analysis method for simultaneously overlapping and fluctuating emitters based on higher-order statistical analysis for separating and localizing the emitters. They have developed a superresolution imaging method which is based on Independent Component Analysis (ICA) and blinking statistics of QDs. They demonstrated that this method is capable of resolving QDs which are closely spaced below the diffraction limit. As pointed out by Lidke et al. under- or over-estimating the number of QDs can affect the accuracy in determination of the loci of the (incorrect number of) emitters. As demonstrated in the current invention (SOFI), no such a priori knowledge of numbers of emitters is necessary. Ventalon et al. in "Dynamic speckle illumination (DSI) microscopy with wavelet pre-filtering", 2007, Optics Letters, vol. 32, pp. 1417-1419, 2007 discuss a statistical analysis method based on linear addition of variances. It is based on the evaluation of fluctuations in the observed signal, but ones which are induced by the excitation light and subsequently evaluated in an analogous way to SOFI. Even though this approach yields sectioning along the optical axis, the fact that the fluctuations are not originating from independent microscopic (i.e. sub-diffraction sized) emitters but from diffraction limited speckles, imposes a fundamental limit on DSI resolution, as it is diffraction limited. The similarities between SOFI and the above mentioned methods have their origin solely in the common mathematical concept of correlation functions. However a detailed analysis of these approaches reveals dramatic differences in capabilities, resulting effects, uses, and applications.

There is therefore a great need for a superresolution and background-reduced imaging method that is simple, fast, low cost, has an intrinsic 3D superresolution capabilities, non-phototoxic, and is well suited for live cell imaging. This method should be flexible and implementable on image stacks acquired by various widely deployed, commercial microscopes and be simple to implement and operate.

BRIEF DESCRIPTION OF THE DRAWINGS

FIG. 2 is a flowchart detailing the protocol for generating a second-order SOFI image.

FIG. 6 is a flowchart detailing the protocol for generating interleaving pixels using cross-cumulants and correcting for the distance factor.

SUMMARY OF THE INVENTION

In this invention, we disclose statistical analysis techniques (based on auto- and cross-correlations/cumulants) of image stacks (movies) of fluctuating objects that improve resolution beyond the classical diffraction limit and reduce the background. The time trajectory of every pixel in the image frame is correlated with itself and/or with the time trajectory of an adjacent pixel. The amplitude of these auto- or cross-correlations/cumulants of each pixel (at a given time lag or averaged or integrated over an interval of time lags) is used as the intensity value of that pixel in the generated superresolved SOFI image. Fields of use include microscopy, telescopy, medical imaging, and other forms of electromagnetical imaging of blinking objects.

Detailed Description of the Invention

Figure 1A:
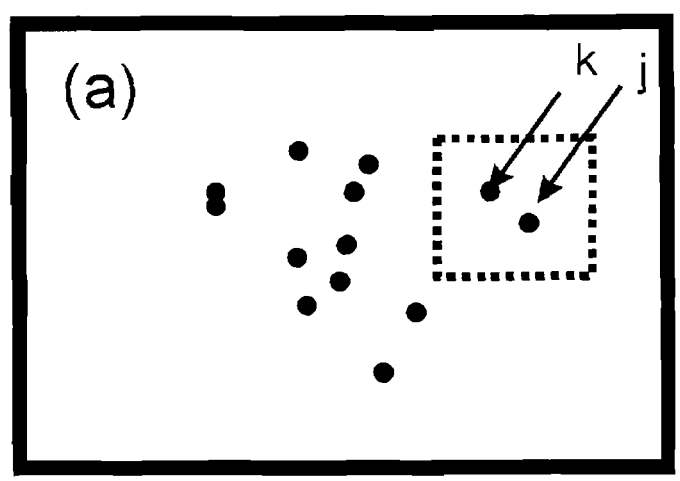
FIGS. 1(a)-1(f) represent the steps required to generate a reduced-background, superresolved image using the SOFI method.

SOFI is a method for imaging a field-of-view comprizing of independently blinking point-like objects (FIG. 1(a)), or structures labeled with such objects. 'Point-like' refers to emitter's dimension much smaller than the dimension of the Point Spread Function (PSF) of the imaging system. Each of the emitters fluctuates (or 'blinks') stochastically and independently (of each other) in one or more of its optical properties, like emission, absorption or scattering. The fluctuations can be intrinsic to the objects or induced by external means, but have to be independent and not synchronized among the objects. The fluctuations can have their origin in a (molecular) transition, in the (molecular) orientation or in (molecular) conformation which causes some optical property to change to a measurable degree. This could for example be due to a transition between two or more energy states of a molecule, or due to a change in an optically polarized emission, absorption, or scattering caused by a molecular dipole reorientation. It is emphasized that the fluctuation (or blinking) need not be of a binary nature like, for example, an 'on' and an 'off' fluorescent states. Any measurable fluctuation could be used for the generation of a SOFI image. In the example, emitters k and j are separated by a distance shorter than the diffraction limit.

Figure 1B:
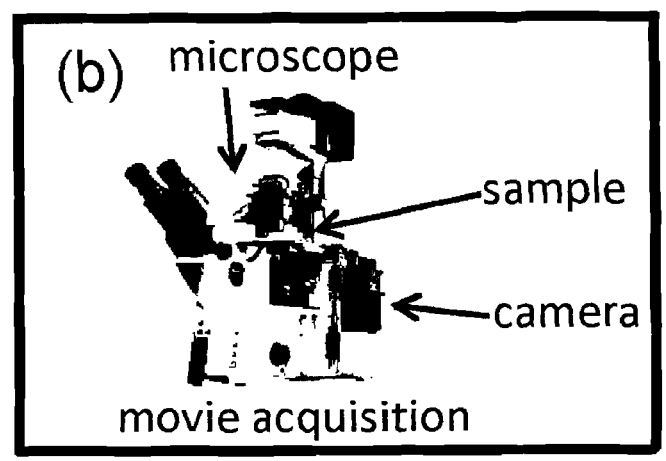
Figure 1C:
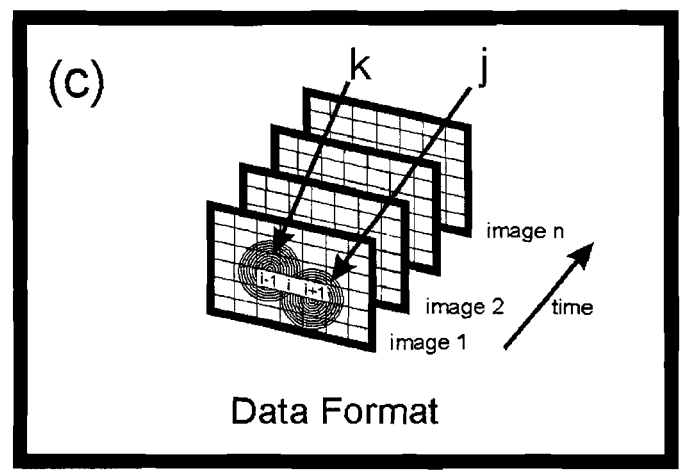

The above mentioned field-of-view (sample, or object plane) is imaged via an optical imaging system (microscope, telescope, etc.) in parallel using a digital camera (or another array detector) or in series (pixel-by-pixel) (FIG. 1(b)), repeatedly (frame-by-frame), over time (i.e. the data is acquired by one of a variety of time-lapse microscopy methods). The signals from emitters k and j (and all other emitters) are intrinsically convolved with the microscope point spread function (PSF) due to the diffraction of light and recorded on a sub-diffraction grid (e.g. pixels of the CCD-camera, or a scanned image) as a function of time. This creates a series of magnified images (a movie, a stack of images, or frames, FIG. 1(c)) of the field-of-view that is detailed in the dotted box of FIG. 1(a). The configuration of the imaging and recording systems are suited and sensitive enough to detect and record the objects' fluctuations (blinking fluorescent emitters in the example) in time and space. The field-of-view is magnified by the imaging system to an extent that one pixel of the recorded image corresponds to a fraction of the PSF's image dimension (i.e. the PSF is sampled, for example, by ~4×4-10×10 pixels).

Figure 1D:
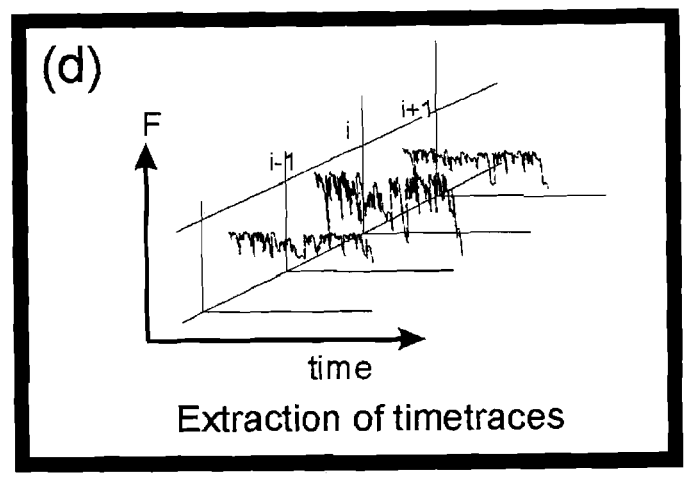

A time trajectory (or a time trace) is extracted for each pixel $r_i=(x_i,y_i,z_i)$ in the recorded image stack, representing (fluorescence) intensity fluctuations as function of time t at that position $r_i$: $F(r_i,t)$ (FIG. 1(d)). i is a discrete index which enumerates all pixels of the array detector. Each pixel's time trajectory is composed of the weighted sum of individual emitters' signals (whose PSFs are contributing to that particular pixel). Shown are time trajectories of three hypothetical pixels i−1, i, i+1, (as noted in FIG. 1(c)) whose time trajectories are the weighted sums of the signals emanating from emitters k and j.

The temporal mean value of $F(r_i,t)$ is calculated and substracted from the recorded time trajectory to yield the zero-mean fluctuation signal: $\delta F(r_i,t)=F(r_i,t)-\langle F(r_i,t)\rangle_t$.

$\left( \langle f(t) \rangle_t = \frac{1}{T} \int_0^T f(t) \, dt \text{ denotes time-averaging} \right)$.

Figure 1E:
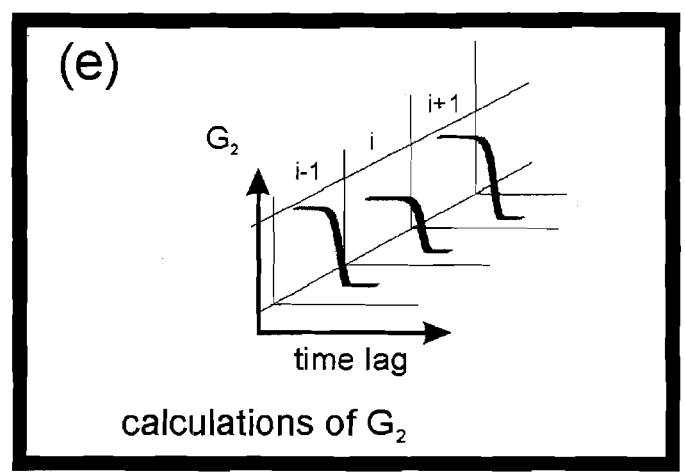
Figure 3A:
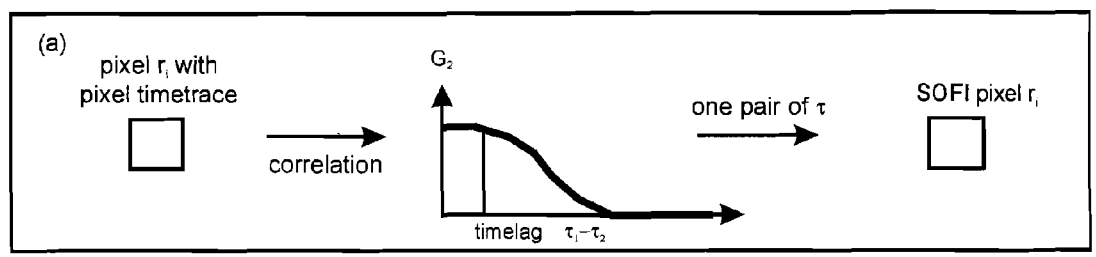
FIGS. 3(a)-3(c) represent various ways for obtaining a SOFI image based on the second-order auto-correlation function, using different time lag configurations.

Subsequently, the temporal second-order autocorrelation function $G_2(r_i,\tau_1,\tau_2)=G_2(r_i,0,1)=\langle \delta F(r_i,t+0)\cdot\delta F(r_i,t+1)\rangle_t$ is calculated for each pixel's time trajectory, resulting a matrix of $G_2(r_i,0,1)$ values. Without loss of generality, we set $\tau_1=0$ and $\tau_2=1$, 0 representing the time point of the first frame of the movie and 1 representing the time lag between two adjacent frames (however, any time lag values for $\tau_1$ and $\tau_2$ within the recorded time range could be chosen) (FIG. 1(e) & FIG. 3(a)). A beneficial outcome of this mathematical operation is the elimination of the uncorrelated background.

Figure 1F:
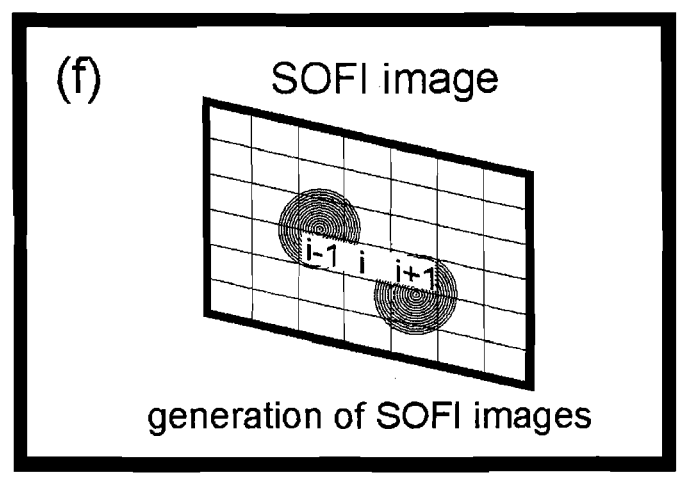

A SOFI image is constructed from the matrix $G_2(r_i,0,1)$ according to:

$$S_2(r_i) = G_2(r_i, 0, 1) = \langle \delta F(r_i, t+0) \cdot \delta F(r_i, t+1) \rangle_t \qquad (1)$$
$$= \sum_k U^2(r_k - r_i)\varepsilon_k^2 \langle \delta s(r_k, t+0) \cdot \delta s(r_k, t+1) \rangle_t$$

where each pixel is assigned the value $S_2(r_i)$ (Eq. (1) and FIG. 1(f)). k extends over all objects/emitters within the sample/field-of-view. Other choices of time lags, or a value of a finite integral of these functions over a chosen range of time lags could be utilized. In the example, emitters k and j are now resolved in the resulted SOFI image.

While the original image (at position $r_i$) was composed of a superposition of point-spread functions (PSFs) of the form $U(r_k-r_i)$ for each object/emitter k, the SOFI image is composed of a superposition of PSFs of the form $U^2(r_k-r_i)$, scaled by a brightness term $\varepsilon_k^2$ and a term representing the temporal fluctuation of each emitter. For an approximated three-dimensional Gaussian PSF:

$$U(r) = \exp\left(-\frac{x^2+y^2}{2\omega_0^2} - \frac{z^2}{2\omega_{0z}^2}\right) \qquad (2)$$

the functional form of the resulted SOFI-modified PSF is:

$$U^2(r) = \exp\left(-\frac{x^2+y^2}{2\tilde{\omega}_0^2} - \frac{z^2}{2\tilde{\omega}_{0z}^2}\right) \qquad (3)$$

where $\tilde{\omega}_0=\omega_0/\sqrt{2}$ and $\tilde{\omega}_{0z}=\omega_{0z}/\sqrt{2}$. As a result, the width of the PSF is reduced by a factor of $\sqrt{2}$ in each of the x, y, and z directions. Often a PSF can be approximately modeled as a three-dimensional Gaussian, justifying the above expression. This holds true for more accurate description of the PSF such as an Airy disk, or the actual experimentally determined PSF. The SOFI-modified PSF still has the form $U^2(r)$, with the resulting contraction in width.

FIG. 2 summarizes the steps of the SOFI algorithm as described paragraphs [0025]-[0030]

EXAMPLE 1

Second Order Auto-Correlation-Based SOFI with Arbitrary Time Lags

The second-order auto-correlation function $G_2(r_i,\tau_1,\tau_2)$ for arbitrary time lags $\tau_j$ is given by:

$$G_2(r_i,\tau_1,\tau_2)=\langle \delta F(r_i,t+\tau_1)\cdot\delta F(r_i,t+\tau_2)\rangle_t \qquad (4)$$

Figure 3B:
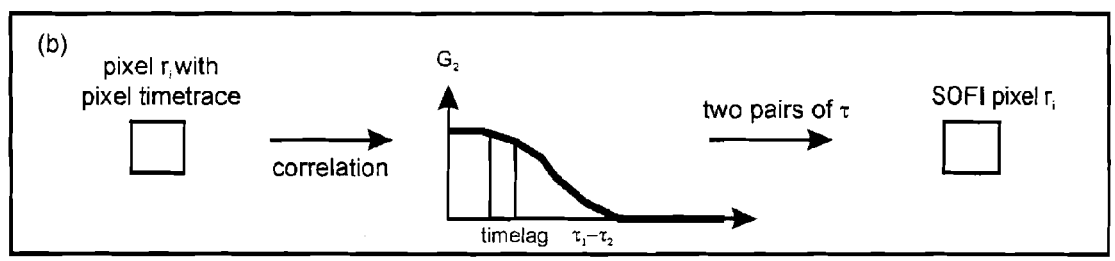
Figure 3C:
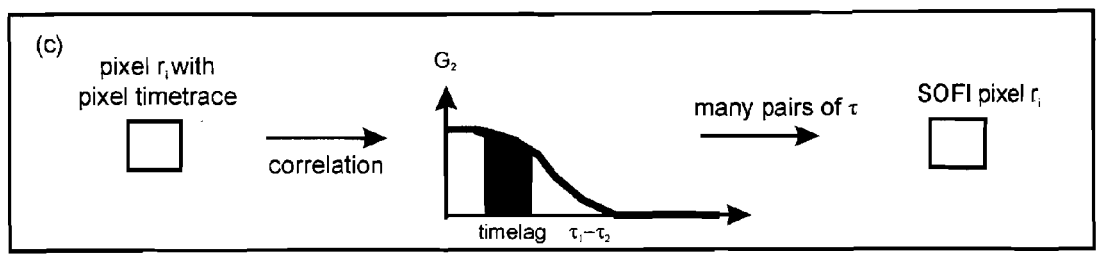

A SOFI image can be generated by using the second-order auto-correlation function not only for time lag $\tau_1=0$ and $\tau_2=1$ as described in paragraph [0028], but for any combination of time lags $\tau_1$, $\tau_2$ (FIG. 3(b)). A superposition of many such combinations will also yield a SOFI image (Eq. (5) and FIG. 3(c)):

$$S(r_i) = \sum_{\tau_1,\tau_2} G_2(r_i, \tau_1, \tau_2) \qquad (5)$$

Note that $\tau_j$ could take finite time lags values or differences between time lags.

EXAMPLE 2

Higher-Order Auto-Cumulant-Based SOFI

The above descriptions of the preferred embodiment and Example 1 (paragraphs [0025]-[0032]) utilize second-order auto-correlations. Higher-order SOFI images could be generated by utilizing the concept of auto-cumulants. Auto-cumulants can be derived from the auto-correlation functions and are identical to them for orders 1, 2 and 3 (the first-order correlation corresponds to the temporal mean value). Higher-order auto-correlation functions (for pixel $r_i$) are computed according to:

$$G_n(r_i,\tau_1,\ldots,\tau_n)=\langle \delta F(r_i,t+\tau_1)\cdot\delta F(r_i,t+\tau_2)\ldots\delta F(r_i,t+\tau_n)\rangle_t \qquad (6)$$

utilizing auto-cumulants (J. Mendel, "Tutorial on Higher-Order Statistics (Spectra) in Signal Processing and System Theory: Theoretical Results and Some Applications",1991, Proceedings of IEEE, vol. 19, no. 3, Equation A-1), $G_n(r_i, \tau_1,\ldots,\tau_n)$ could be computed according to Eqs. (7) below that describe the relationship between auto-cumulants $C_n$ and auto-correlations $G_n$ (only relationships up to 4th order are shown):

$$C_2 = (r_i, \tau_1, \tau_2) = G_2(r_i, \tau_1, \tau_2) \qquad (7)$$
$$C_3(r_i, \tau_1, \tau_2, \tau_3) = G_3(r_i, \tau_1, \tau_2, \tau_3)$$
$$C_4(r_i, \tau_1, \tau_2, \tau_3, \tau_4) =$$
$$G_4(r_i, \tau_1, \tau_2, \tau_3, \tau_4) - G_2(r_i, \tau_1, \tau_2)G_2(r_i, \tau_3, \tau_4) -$$
$$G_2(r_i, \tau_1, \tau_3)G_2(r_i, \tau_2, \tau_4) - G_2(r_i, \tau_1, \tau_4)G_2(r_i, \tau_2, \tau_3)$$

similarly to Eq. (5), a higher order SOFI image could be constructed by assigning the value of a superposition of higher-order cumulants $S_n(r_i)$ to the corresponding pixels:

$$S_n(r_i) = \sum_{\tau_1,\ldots,\tau_n} C_n(r_i, \tau_1, \ldots, \tau_n) \qquad (8)$$

and similarly to Eq. (1), this higher-order SOFI image will have the form:

$$S(r_i) = \sum_k U^n(r_k - r_i)\varepsilon_k^n w_k(\tau_1, \ldots, \tau_n) \qquad (9)$$

with the original PSFs raised to the n-th power $U^n(r_k-r_i)$ and multiplied by the brightness factor $\epsilon_k^n$ and the temporal weighting factor $w_k(\tau_1, \ldots, \tau_n)$. For a 3D Gaussian PSF approximation, the PSF's width improves by a factor of $\sqrt{n}$. For a more accurate approximation of the PSF (Airy disk, or the experimentally determined PSF), the resulting resolution improvement is determined by the relative widths of $U^n(r)$ and $U(r)$.

EXAMPLE 3

Second-Order Cross-Correlation-Based SOFI

Analogous to the second-order auto-correlation SOFI scheme (paragraphs [0025]-[0031]), one can define a spatio-temporal second-order cross-correlations-based SOFI approach. In this case, different pixels' $r_{i1}$ and $r_{i2}$ time trajectories are correlated at time lags $\tau_1=0$ and $\tau_2=1$. The second-order cross-correlation $XG_2$ is then given by (see FIG. 4($a$)):

$$XG_2(r_{i1}, r_{i2}|0,1) = \langle \delta F(r_{i1}, t+0) \cdot \delta F(r_{i2}, t+1) \rangle_t \tag{10}$$

Whenever the original PSF is oversampled by several pixels, and those pixels record fluctuations from near-by emitters in a correlated manner, a cross-correlation could be calculated. Although time trajectories of different pixels are used to calculate the cross-correlation terms, the value of $XG_2$ could be assigned to a particular SOFI image's pixel according to:

$$XG_2(r_{i1}, r_{i2}|0, 1) = \tag{11}$$
$$U\left(\frac{r_{i1}-r_{i2}}{\sqrt{2}}\right) \cdot \sum_k U^2\left(r_k - \frac{r_{i1}+r_{i2}}{2}\right) \cdot \epsilon_k^2 \langle \delta s_k(t+0) \cdot \delta s_k(t+1) \rangle_t$$

where k extends over all emitters present in the field-of-view/sample and $r_k$ represents emitter k's positions. $r_{i1}$ and $r_{i2}$ represent the pixels time trajectories' positions used for the cross-correlation. The value of $XG_2$ is assigned to the position $$r = \frac{r_{i1}+r_{i2}}{2}$$

(i.e. the geometric center of $r_{i1}$ and $r_{i2}$) in the final SOFI image. The assigned SOFI's pixel intensity is given by:

$$S_2(r) = \frac{XG_2(r_{i1}, r_{i2}|0, 1)}{U\left(\frac{r_{i1}-r_{i2}}{\sqrt{2}}\right)} \tag{12}$$

By setting $r_{i1}=r_{i2}$ and normalizing the PSF ($U(0)=1$) in Eq. (12) the auto-correlation result (Eq. (1)) is recovered.

EXAMPLE 4

Second-Order Cross-Correlation-Based SOFI with Arbitrary Time Lags

As in Example #1, the second-order cross-correlation approach can be extended to arbitrary time lags $\tau_j$:

$$XG_2(r_{i1}, r_{i2}|\tau_1, \tau_2) = \langle \delta F(r_{i1}, t+\tau_1) \cdot \delta F(r_{i2}, t+\tau_2) \rangle_t \tag{13}$$

Figure 4A:
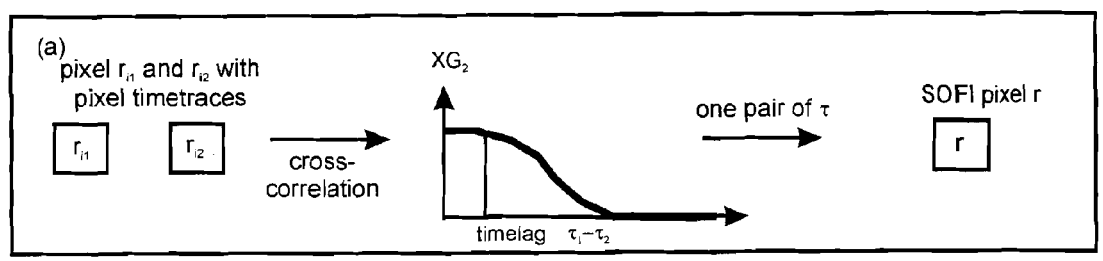
FIGS. 4(a)-4(c) represent various ways for obtaining a SOFI image based on the second-order cross-correlation function, using different time lags configurations.
Figure 4B:
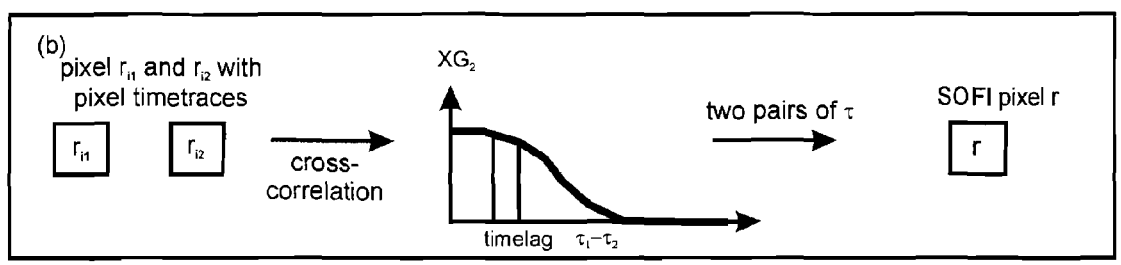
Figure 4C:
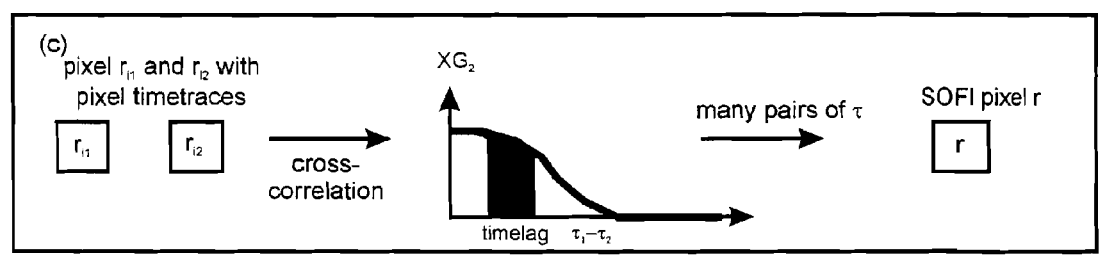

A SOFI image can be generated by using the second-order cross-correlation function not only for time lags $\tau_1=0$ and $\tau_2=1$ as described in Example 3, but for any combination of time lags $\tau_1, \tau_2$ (FIG. 4($b$)). A superposition of many such combinations will also yield a SOFI image (Eq. (14) and FIG. 4($c$)):

$$S_2(r) = \sum_{\tau_1, \tau_2} \frac{XG_2(r_{i1}, r_{i2}|\tau_1, \tau_2)}{U\left(\frac{r_{i1}-r_{i2}}{\sqrt{2}}\right)} \tag{14}$$

Note that $\tau_j$ could take finite time lags values or differences between time lags.

EXAMPLE 5

Multiple Ways for Calculating Second-Order Cross-Correlation-Based SOFI

Since the location of a second-order cross-correlation-based SOFI pixel is assigned to the location of the geometric center of the two pixels $r_{i1}$ and $r_{i2}$ $$r = \frac{r_{i1}+r_{i2}}{2}$$

Figure 9A:
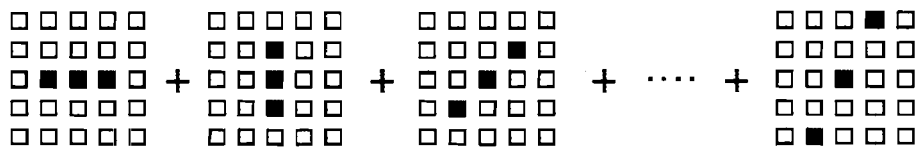
FIGS. 9(a)-9(b) show how to obtain the same SOFI pixel by cross-correlating various pixels' time trajectories.
Figure 9B:
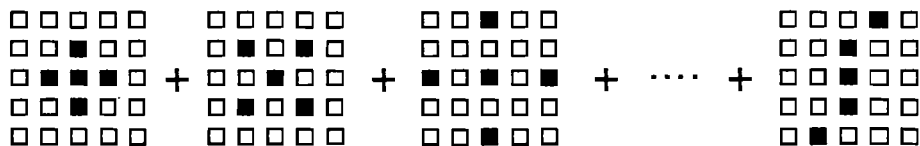

(FIG. 5($a$)), and since other combinations of pixel pairs could have the same geometric center (FIG. 9($a$)), it would be most efficient to utilize pairs where $\|r_{i1}-r_{i2}\|$ is on the order of, or smaller than, the width of the PSF. The SOFI image would then take the form:

$$S_2(r) = \sum_{r_{i1}+r_{i2}=2r} \frac{XG_2(r_{i1}, r_{i2}|\tau_1, \tau_2)}{U\left(\frac{r_{i1}-r_{i2}}{\sqrt{2}}\right)} \tag{15}$$

EXAMPLE 6

Higher-Order Cross-Cumulant-Based SOFI

Analogous to the higher-order temporal auto-cumulant approach (Example 2), it is possible to define a higher-order spatio-temporal cross-cumulants SOFI approach, in which the time trajectories of different pixels are cross-correlated. Cross-cumulants can be derived from cross-correlation functions and are identical to them for orders 2 and 3. Higher-order spatio-temporal cross-correlation functions $XG_n$ have as inputs n-tupel pixels' time trajectories ($r_{i1}, r_{i2}, \ldots, r_{in}$) and n-tupel time lags ($\tau_1, \tau_2, \ldots \tau_n$). $XG_n$ is given by:

$$XG_n(r_{i1}, \ldots, r_{in}|\tau_1, \ldots, \tau_n) = \langle \delta F(r_{i1}, t+\tau_1) \cdot \delta F(r_{i2}, t+\tau_2) \ldots \delta F(r_{in}, t+\tau_n) \rangle_t \tag{16}$$

and could be computed utilizing cross-cumulants (J. Mendel, "Tutorial on Higher-Order Statistics (Spectra) in Signal Processing and System Theory: Theoretical Results and Some Applications", 1991, Proceedings of IEEE, vol. 19, no. 3, Equation A-1). $XG_n(r_{i1}, \ldots, r_{in}|\tau_1, \ldots, \tau_n)$ could be computed according to Eqs (17) below that describe the relationship between cross-cumulants $XC_n$ and cross-correlations $XG_n$ (only relationships up to the fourth-order are shown):

$$XC_2(r_{i1}, r_{i2}, \tau_1, \tau_2) = XG_2(r_{i1}, r_{i2}, \tau_1, \tau_2) \quad (17)$$

$$XC_3(r_{i1}, r_{i2}, r_{i3}, \tau_1, \tau_2, \tau_3) = XG_3(r_{i1}, r_{i2}, r_{i,3}, \tau_1, \tau_2, \tau_3)$$

$$XC_4(r_{i1}, r_{i2}, r_{i3}, r_{i4}, \tau_1, \tau_2, \tau_3, \tau_4) =$$
$$XG_4(r_{i1}, r_{i2}, r_{i3}, r_{i4}, \tau_1, \tau_2, \tau_3, \tau_4) -$$
$$XG_2(r_{i1}, r_{i2}, \tau_1, \tau_2) XG_2(r_{i3}, r_{i4}, \tau_3, \tau_4) -$$
$$XG_2(r_{i1}, r_{i3}, \tau_1, \tau_3) XG_2(r_{i2}, r_{i4}, \tau_2, \tau_4) -$$
$$XG_2(r_{i1}, r_{i4}, \tau_1, \tau_4) XG_2(r_{i2}, r_{i3}, \tau_2, \tau_3)$$

Whenever the image of the original emitters' PSF is large enough to be oversampled by several pixels, and those pixels can detect correlated fluctuations, a cross-correlation can be performed between pixels which mutually oversample a region. Each cross-cumulant calculated can be used to generate a SOFI image. Even though the cross-cumulants feature different pixels' time trajectories as an input, it is possible to assign a unique location (pixel) for the resulted cross-cumulant value in the final SOFI image. $XC_n$ is given by:

$$XC_n(r_{i1}, \ldots r_{in} | \tau_1, \ldots, \tau_n) = \quad (18)$$
$$\prod_{l<j}^{n} U\left(\frac{r_{il}-r_{ij}}{\sqrt{n}}\right) \cdot \sum_k U^n\left(r_k - \frac{1}{n}\sum_{m=1}^{n} r_{im}\right) \cdot \varepsilon_k^n \cdot w_k(\tau_1, \ldots, \tau_n)$$

The location of the corresponding SOFI pixel is given by:

$$r = \frac{1}{n}\sum_{m=1}^{n} r_{im} \quad (19)$$

(as can be seen from Eq. (18)). The higher order cross-cumulants SOFI image is given by:

$$S_n(r) = \frac{XC_n(r_{i1}, \ldots r_{in} | \tau_1, \ldots, \tau_n)}{\prod_{l<j}^{n} U\left(\frac{r_{il}-r_{ij}}{\sqrt{n}}\right)} \quad (20)$$

Analogous to Eq. (14) a superposition of many time lags combinations can be used to calculate the higher order cross-cumulants SOFI image:

$$S_n(r) = \sum_{\tau_1,\ldots,\tau_n} \frac{XC_n(r_{i1}, \ldots r_{in} | \tau_1, \ldots, \tau_n)}{\prod_{l<j}^{n} U\left(\frac{r_{il}-r_{ij}}{\sqrt{n}}\right)} \quad (21)$$

Since the location of the $n^{th}$-order cross-cumulant-based SOFI pixel is assigned to the location of the geometric center of the n pixels $$r = \frac{1}{n}\sum_{m=1}^{n} r_{im}$$

and since other combinations of pixels tupel could have the same geometric center, it would be most efficient to utilize tupel where $\|r_{i1}-r_{ij}\|$ (for all combinations (l,j)) is on the order of, or smaller than, the width of the PSF. The SOFI image would then take the form:

$$S_n(r) = \sum_{r_{i1}+\ldots+r_{in}=2r} \frac{XC_n(r_{i1}, \ldots r_{in} | \tau_1, \ldots, \tau_n)}{\prod_{l<j}^{n} U\left(\frac{r_{il}-r_{ij}}{\sqrt{n}}\right)} \quad (22)$$

The resulting higher-order SOFI image contains a combination of PSFs of the form $U^n(r_k-r)$, with a brightness factor $\varepsilon_k^n$ and a temporal weighting factor $w_k(\tau_1, \ldots, \tau_n)$. For a 3D Gaussian PSF approximation, the PSF's width improves by a factor of $\sqrt{n}$. For a more accurate approximation of the PSF (Airy disk, or the experimentally determined PSF), the resulting resolution improvement is determined by the relative widths of $U^n(r)$ and $U(r)$.

EXAMPLE 7

Generating Interleaved Pixels by Cross-Cumulants

Figure 5A:
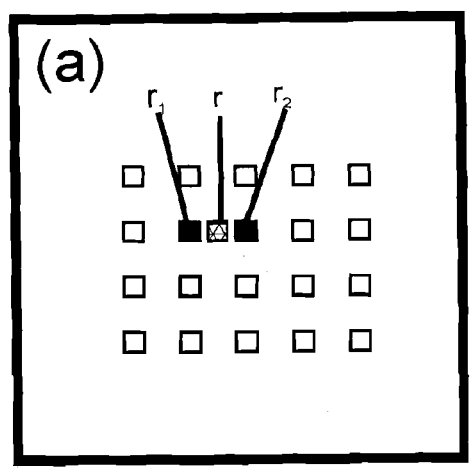
FIGS. 5(a)-5(c) show the principle of generating interleaving pixels, in between physical pixels, for a SOFI image (shown is an example for the particular second-order cumulant case).
Figure 5B:
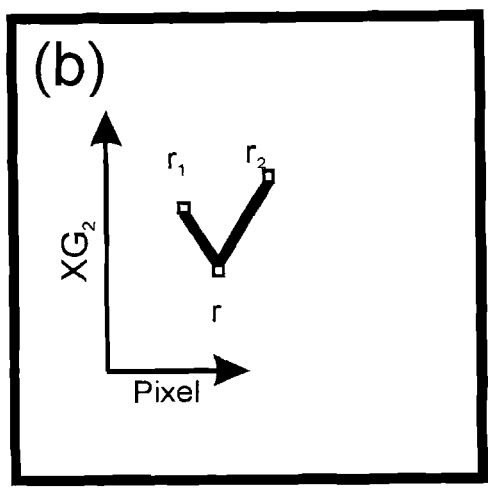
Figure 5C:
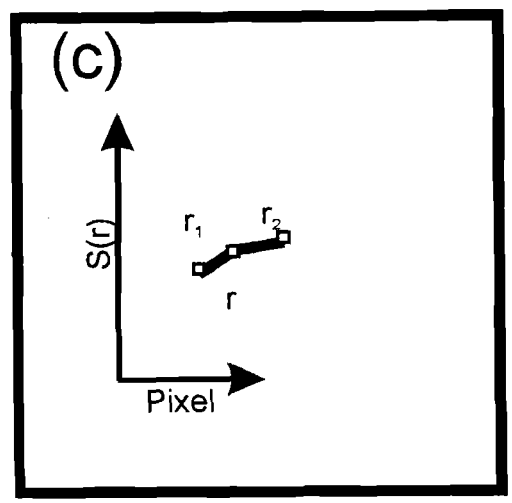
Figure 7A:
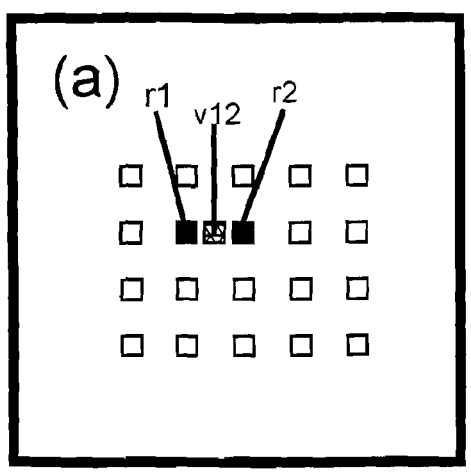
FIGS. 7(a)-7(d) show an example of which pixels' time trajectories can be cross-correlated in order to obtain a fully up-sampled second-order SOFI image.
Figure 7B:
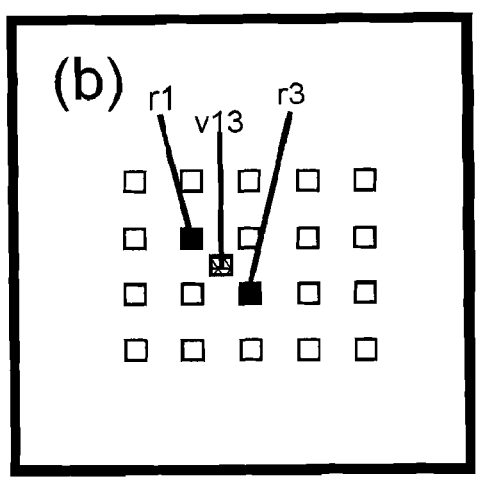
Figure 7C:
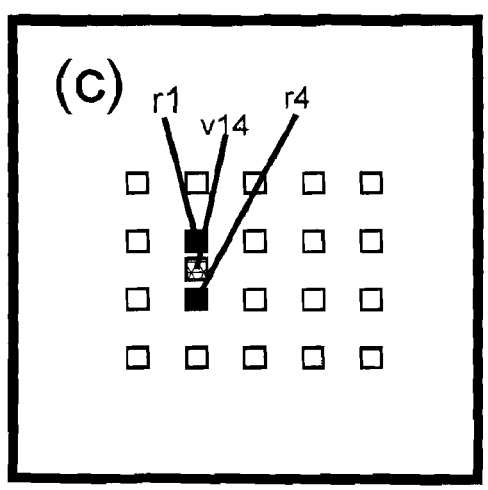
Figure 7D:
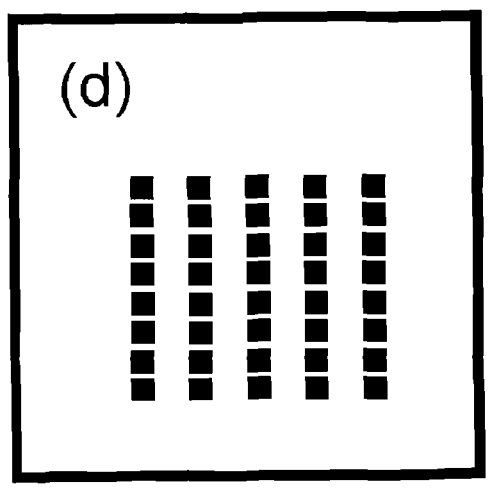

Interleaving pixels could be generated by cross-correlating trajectories of pixels whose geometric center falls in between physical ('real') pixels. FIG. 5(a) shows how to generate an interleaved pixel by second-order cross-correlation. Two adjacent pixels' time trajectories are cross-correlated, resulting in an interleaved pixel located in between the two physical pixels. For example, a second-order cross-correlation between a pixel time trajectory at coordinate $r_1=100$ and a pixel time trajectory at coordinate $r_2=101$ produces a pixel at coordinate r=100.5. This approach holds true also for higher order cumulants. The cross-cumulant is weighted by a factor which is dependend on the distances of the pixel time trajectory used for the generation of the cross-cumulant (FIGS. 5(b) & 5(c)):

$$\prod_{l<j}^{n} U\left(\frac{r_{il}-r_{ij}}{\sqrt{n}}\right) \quad (23)$$

This distance factor (Eq. (23)) has to be known for each pixel in the SOFI image. Then the SOFI value for all pixels can be calculated according to Eq. (20), resp. Eq. (21) resp. Eq (22) (see also FIG. 5(c)). Considering the possible combinations of neighboring pixels, a second-order cross-correlation calculation between neighboring pixels creates effective pixels halfway between each horizontal, vertical, and diagonal pairing (FIG. 6 and FIGS. 7(a)-7(d)). Likewise, the higher order cross-correlations produce even larger numbers of effective pixels given by each possible pairing. For example the fourth-order cross-cumulant allows the pairing of 4 different pixels' time trajectories.

Figure 8:
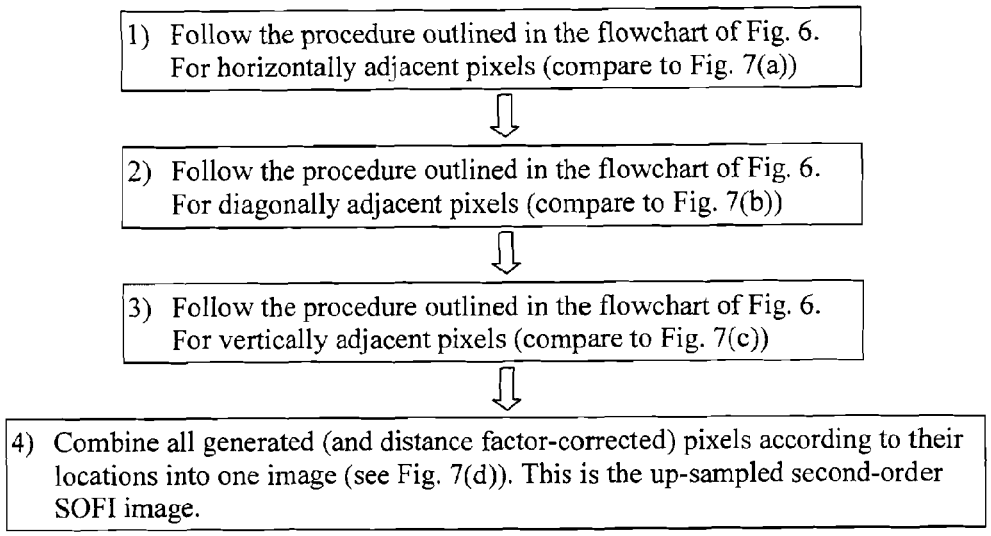
FIG. 8 is a flowchart detailing the protocol for generating an up-sampled second-order SOFI image using second-order auto- and cross-correlations.

In contrast to interpolation, these cross-cumulant derived interleaved pixels provide true increased resolution. For example, a pair of emitters which is spaced closer than the pixel sampling size (and therefore not resolved in the original, conventional image) can be resolved by using cross-correlations/cross-cumulants to produce a sufficient number of SOFI pixels so that an intensity dip in between two intensity peaks (representing the two emitters) becomes visible. As a result, by using the cross-correlation approach in combination with the auto-correlation approach across multiple cumulant orders, it is possible to create continually increasing numbers of pixels in the resulting image, allowing a single image stack to produce SOFI images with a range of resolutions, a range of numbers of resulting pixels, and resolution exceeding even the original pixel sampling size. In general, the cross-correlation approach has the advantage that even though the PSF is shrinking in size, the sampling frequency which has to be used to record the SOFI image (e.g. the effective pixel size of the camera: nm/pixel) does not have to be adjusted. The original sampling frequency with respect to the PSF could be maintained. A flowchart of the generation of such up sampled SOFI images can be found in FIG. 8, demonstrating this second order technique.

EXAMPLE 8

Signal Enhancement by Cross-Cumulants

Cross-cumulants can be used to calculate the SOFI value of a pixel (virtual or real) multiple times using different pixel-time trajectory pairs (respective pixel-time trajectory triples or n-tupels for the $n^{th}$-order SOFI image). This approach can be used to enhance a noisy signal, since each cross-cumulant will carry the same information but obtained from different pixel-time trajectory pairs (respective pixel time trajectory-triples or n-tupels for the $n^{th}$ order SOFI image). Which pixel time trajectory has to be cross-correlated can be seen from Eq. 19. For example, see FIGS. 9(a) and 9(b).

EXAMPLE 9

Microscopy Applications

SOFI is particularly suited for fluorescence microscopy applications. It can be used to produce superresolution and background reduction on almost any fluorescence microscope and with any fluorophore which independently transitions between two or more intensity, lifetime, polarization, or spectral states. Examples of such fluorophore transitions include quantum dot blinking, fluorophore triplet states during which they do not emit, and photoswitchable probes which have a probability of turning off or changing spectra under a specific wavelength (and possibly low intensity) illumination.

The SOFI approach is notable in comparison to other superresolution techniques since it works on a wide variety of standard fluorescence microscopes with no need for modification to the instrument. This is possible because the key to the resolution enhancement is the stochastically independent blinking/fluctuations of the emitters. The microscope must only provide the means to record an image stack of these emitters so that their blinking/fluctuations could be analyzed. As a result, SOFI can be performed on widefield microscopes where a camera is used to image an entire field of view simultaneously. It can also be used on modified widefeld microscopes such as a confocal spinning disc microscope, where sectioning and elimination of out of focus light is improved by a spinning disk of pinholes, and on Total Internal Reflection Fluorescence (TIRF) microscopes, where internal reflection at the coverslip is used to select a very narrow illumination slice (close to the glass surface), causing a very narrow PSF in the depth (z) direction. In each case, the microscope provides the initial (diffraction-limited) PSF, and subsequent utilization of the SOFI algorithm provides superresolution in all three dimensions as well as background reduction.

The SOFI approach can also be used on a raster scanning setup in which a single excitation spot is scanned through the sample (scanning beam or scanning stage) to produce an image. This can be accomplished by simply scanning slow enough so that fluctuations could be observed at a single point. Alternatively one can try to sample the fluctuations by scanning the sample multiple times, so quickly that the beam returns to the same point fast enough to over-sample fluctuations with respect to the fluctuation rate (i.e. fast enough so that the signal is still sufficiently correlated in time). Even a third option could be used: the combination $\tau_j=0$ for all j (see also [0047]). For this approach the temporal correlation can be lost completely. However, it will not be possible to apply the cross-cumulant approach anymore.

EXAMPLE 10

Non-Fluorescent Microscopy Applications

SOFI can be performed on all kinds of objects that blink/fluctuate in their electromagnetic emission, absorption or scattering properties. For example, a stochastically reorienting/rotationaly diffusing small gold nano-rod nanoparticle will scatter light anisotropically. A wide-, dark-field microscope equipped with polarization optics and a suitable camera could image and record fluctuations in light scattering of such reorienting objects and acquire a SOFI-compatible data set. Similarly, changes in absorption dipole orientation could be exploited and subjected to SOFI analysis.

EXAMPLE 11

Non-Microscopy Applications

SOFI applications are not limited to microscopy. Any electromagnetic far-field imaging system or wave phenomena that is subjected to the diffraction limit, that records signals from fluctuating point-like emitting/absorbing/scattering sources could take advantage of the SOFI algorithm. Possible applications include telescopy, medical imaging, and other forms of electromagnetical imaging.

EXAMPLE 12

Selection of Time-Lags, Blinking Timescale, Shot Noise, Frame Rate, and Image Stack Duration The correlation function works for any arbitrary time lag $\tau_j$, or relative time delays between signal values which are correlated. However, a careful matching between the typical fluctuation/blinking timescale (rate), the image acquisition frame rate, and the chosen correlation time lag is necessary for correct implementation of the SOFI algorithm. It also impacts the inclusion or removal of usually unwanted short timescale detector fluctuations such as afterpulsing, the tendency in some detectors to produce counts shortly after other counts, or shot noise, which is the uncorrelated statistical fluctuation in signal intensity from one frame to the immediately following one.

The simplest selection of time lags is to set all $\tau_j=0$, which makes the correlation functions equivalent to the mean-centered moments, and the generalized cumulants equal to the more conventional cumulants. For example, under this special case the second-order SOFI image is equivalent to the temporal variance of each pixel. This is conceptually simplest, and it permits the observation of very short timescale fluctuations; however, it results in the inclusion of shot noise behavior which reduces the ability to resolve independently fluctuating emitters. The shot noise can be removed after the fact if it obeys a known behavior, such as the measured noise distribution of a camera, or the Poisson-distributed shot noise of a photon counting detector. Removal of the shot noise in this manner allows the sensitivity to short timescale fluctuations of the emitters while still obtaining superresolution.

However, a SOFI image can be generated which is intrinsically shot-noise free, if one or more non-zero time lags are chosen. This approach is guaranteed to suppress the shot-noise contribution regardless of its actual statistical distribution. Once non-zero time lags are used, it is necessary to consider the timescale of the intrinsic blinking behavior exhibited by the emitters. For obtaining good sensitivity in observing blinking behavior with this approach, the typical blinking timescle should be long enough so that one blinking period ('off' time) usually persists across more than one integration time per frame (the inverse of the frame rate) of the original image stack.

When cross-correlations between independent pixels is used (instead of auto-correlations), shot noise fluctuations are suppressed even for zero time lag. Thus, by using either a subtraction of the shot-noise distribution (when using auto-correlations) or a cross-correlation approach with zero time lag, it is possible to look at blinking timescales as short as the acquisition time of a single frame, which could be shorter than the inverse of the frame rate, as for example, by using strobed excitation (whereby the illumination which excites the fluorescent emitters is only turned on for a brief time during each frame, allowing the generation of SOFI images from blinking timescales much shorter than the frame rate). This approach could, for example, be used to image short timescale triplet state behavior where a fluorophore blinks by entering a non-emitting triplet state for a duration of microseconds to milliseconds.

The other critical aspect of selecting a timescale for analysis is for the prevention of slow timescale drifts in the mean (as for example, due to slow thermal or mechanical drifts of the sample stage) disrupting the generation of a SOFI image. This is resolved by either generating the correlation functions in segments much shorter than the drift time-scale so that the mean is centered for each segment, or by adding uncorrelated random noise to normalize the means. For example, fluorescence samples with dyes commonly experience bleaching, where the fluorophores have a certain probability with each excitation of permanently entering a dark state. This results in the mean intensity exhibiting an exponential decay where, depending on the fluorophore and excitation power, the decay time can range from seconds to many minutes or longer. Since all regions of the image with that dye will bleach similarly, this makes many emitters, which for SOFI should be independent, effectively correlated with each other in that they will transition from a brighter state at the beginning of the image stack toward a dark state at the end of the image stack. By splitting the image stack into a set of shorter stacks, or using the random noise solution, this problem could be mitigated.

EXAMPLE 13

Stacks of Image Stacks-Generating SOFI Movies

The speed of acquiring a SOFI image is given by the imaging system and the timescale of the fluctuations. Therefore one can acquire multiple image stacks and generate SOFI image sequences (SOFI movies) featuring superresolution. Specifically, when the object which is imaged is moving, the potentially short acquisition times prove advantageous, because otherwise a blurred superresolution image could result. The calculation of SOFI images can be done very efficiently and quickly using either software or hardware-implemented approaches.

EXAMPLE 14

Background Reduction

The generation of a SOFI image relies on the analysis of temporal signal fluctuations relative to the mean signal level. As a result, background signals which remain constant or which produce very little fluctuation are suppressed, resulting in background-reduced (and sometimes even background-free) and contrast-enhanced SOFI images. This background reduction can remove very large constant signals, allowing a much smaller fluctuating signal to become visible. This can permit the observation of structures (superresolved or larger) which would otherwise be lost or invisible in a large background.

When a time-lag selection greater than zero is chosen, the contrast enhancement selects only signals which persist in a pixel across more than one frame of the original image stack. As a result, shot noise, as part of the background, is reduced, as are many other signals which are much shorter than the duration of the frame. Cross-correlation also reduces any fluctuating background which is present only in a single pixel, for example detector afterpulsing, cosmic rays, dark counts, and shot noise even for zero time lag, and it selects for contrast enhancement only the fluctuations which happen in a correlated manner across multiple pixels.

In the case of cellular imaging with fluorescence, a common problem which disrupts image quality is the high degree of background provided by both out of focus light and cell autofluorescence (where the natural contents of the cell emit some light in response to the excitation light). As both out of focus light and cell autofluorescence are non-fluctuating signals, they are eliminated in the SOFI image, producing images of substantially higher quality and solving an important contrast problem in cellular imaging.

Out of focus light and scattering significantly contribute to reduced contrast and reduced imaging performance in live animals or tissue imaging, The same principle described above for cellular imaging applies here too; the background reduction and contrast enhancement of SOFI can greatly aid such in-vivo applications.

EXAMPLE 15

3-Dimensional (3D) Imaging

The SOFI approach intrinsically shrinks the PSF in all 3 dimensions. It is therefore possible to achieve three-dimensional superresolution. In fact, even a two-dimensional SOFI image has increased resolution in the z dimension since it enhances the signals coming from emitters that are closer to the focal plane. A 3D superresolved stack is obtained by simply acquiring image stacks at each of several different depths (sections), and calculating a SOFI image for each section, resulting in a 3D superresolved and background reduced SOFI image stack.

Interleaving pixels along the z dimension can be calculated as in Example #7 by cross-correlation signals originating from different sections or by interpolating the image stacks to intermediate sections prior to implementing the SOFI algorithm. However, this introduces requirements for the timescale of imaging. To obtain intermediate pixels, the frames at each depth must be measured either simultaneously or fast enough so that the correlation between frames of different depths is preserved.

To obtain a 3D SOFI image with a cross-correlation between pixels at different depths, one would need to measure the signal at two depths either simultaneously or in tandem, but fast enough relative to the fluctuations time scale (so that the correlation is preserved).

Reduction to Practice

Figure 10:
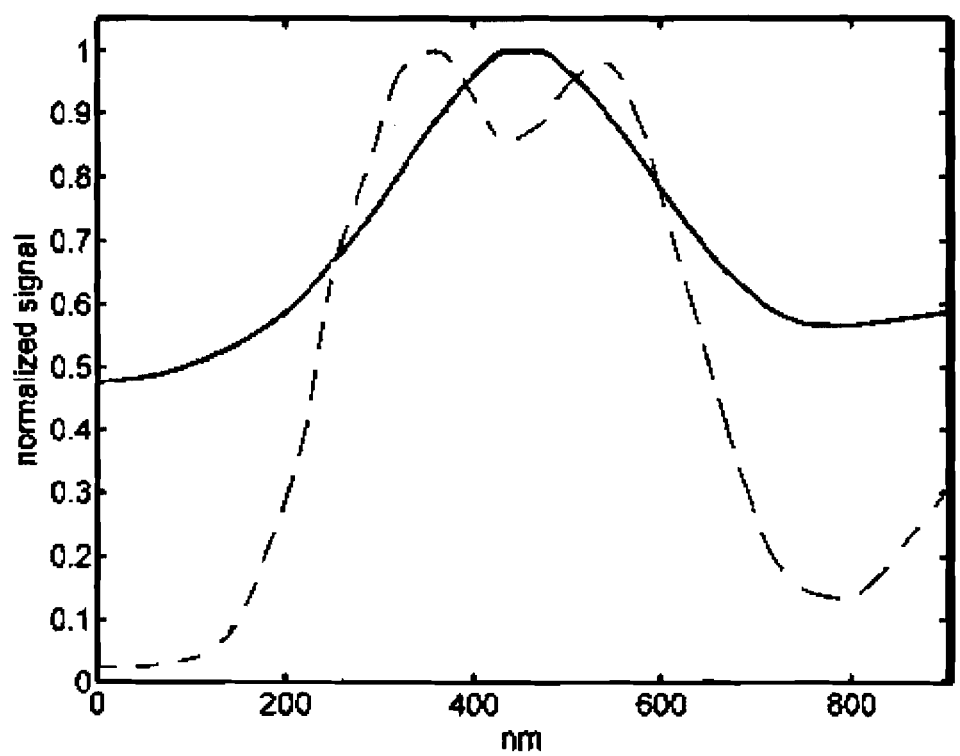
FIG. 10 compares the resolution enhancement of SOFI to that of a conventional wide-filed microscopy.

Dertinger T et al., "Fast, background-free, 3D super-resolution optical fluctuation imaging (SOFI)", 2009, Proceedings of the National Academy of Sciences, vol. 106, pp. 22287-22292 give a detailed description of SOFI implementation and reduction to practice. Below we give a brief summary: microtubules of 3T3 fibroblast cells were immunostained with quantum dots (QDs), imaged in a wide-field microscope with a CCD camera, and the data stack was analysed by the SOFI algorithm. The resulted cross-section of the superresolved and background-reduced SOFI image (Figs. E-H of above mentioned reference) is shown in FIG. 10. Listed below are the details for obtaining the SOFI image.

Cell Labeling: NIH-3T3 (ATCC, Manassas, Va., USA) cells were grown up to a confluence level of ~80% in Dulbecco's Modified Eagle's Medium (ATCC, Catalog No. 30-2002) plus 10% fetal calf serum (10082-147, Invitrogen, Carlsbad) plus 100 units penicillin-streptomycin (Pen-Strep, 15140122, Invitrogen, Carlsbad). For fixation the following procedure has been applied. Cells were incubated at RT for 15 min with CB buffer (10 mM MES, pH6.2, 140 mM NaCl, 2.5 mM EGTA, 5 mM $MgCl_2$), 11% Sucrose, 3.7% paraformaldehyde, 0.5% glutaraldehyde, 0.25% Triton as a fixative. Quenching was done with 0.5 mg/ml sodium borohydride in CB for 8 min. Cells were washed once with PBS and blocked in 2% BSA+PBS for 1 hour at RT. Microtubules were stained using 1:500 dilution of DM1A anti-α-tubulin monoclonal Antibody (Sigma Inc.) in 2% BSA+PBS. Cells were then washed 3 times with PBS and incubated for 1 h at RT with a 1:400 dilution of quantum dots (QDs) QD625 labeled goat $F(ab)_2$, anti-mouse IgG Antibodies (H+L) (Invitrogen Inc., Carlsbad) in 6% BSA+PBS. Cells were washed 3 times with PBS. All steps were performed in a humidity chamber. Specimens were dehydrated by floating the coverslips sequentially for 5 seconds in 30%, 70%, 90% and 100% ethanol. Subsequently they were gently spin-coated (~500 rpm) with 1 mg/ml PVA.

Microscope Setup: Movies were taken on an inverted wide-field microscope (Olympus, IX71). A 470 nm LED array device was used as a light source (Lumencor Inc., Aura Light Engine, Beaverton, Oreg., USA). Sample excitation and fluorescence collection was done using a high numerical aperture objective (Olympus, UPlanApo 60×, 1.45, Oil, Center Valley, Pa., USA). Excitation light was filtered from fluorescence using a 620/40 bandpass emission filter (D620/40, Chroma Technology Corp, Rockingham, Vt., USA). The fluorescence light was focused on a CCD camera (Andor, $iXon^{EM}$+885, Belfast, Northern Ireland). Magnification was adjusted to obtain 35 nm/pixel.

Data Acquisition: A movie was acquired with 3000 frames, 100 ms/frame.

Data Analysis: Movies were analyzed using the SOFI algorithm described in paragraphs [0025]-[0031] above using a custom written Matlab software.

FIG. 10. Compares the resolution enhancement of SOFI. Intensity profiles extracted from the dotted lines in FIG. 5 E-H of Dertinger T et al. The solid line indicates a cross-section in the original wide-field image. The dashed line indicates the same cross-section in the second-order SOFI image. This comparison clearly establishes gain in resolution and reduction in background.

What is claimed is:

1. A computer program stored on a non-transitory medium which, when executed by a processor, performs a method for analyzing a field-of-view of independently blinking objects, comprising the following steps:
   i) selecting a sample or an observation image comprised of objects from the class of optically signaling objects that stochastically and independently fluctuate;
   ii) acquiring a sequence of optical images of the object as a function of time, producing an x, y, t image stack of pixels;
   iii) calculating at least one of: an autocorrelation function, an autocumulant function, a crosscorrelation function, or a crosscumulant function from the temporal fluctuations of selected pixels of the image stack to at least the second order for at least a chosen time lag or a plurality of chosen time lags;
   iv) generating a superresolved and background-reduced image including pixels having an intensity value being the amplitude of the function for the at least one chosen time lag or a linear combination of amplitudes of the functions for different chosen time lags.

2. The computer program according to claim 1, wherein the independently blinking objects could be separated by distances shorter than the diffraction limit -resolved distance of the imaging system used.

3. The computer program according to claim 1, wherein the sample objects comprising the sample or the observation image are selected from the class comprising emitting, absorbing or scattering materials and objects labeled with such materials.

4. The computer program according to claim 1, wherein the sequence of optical images is produced from a scanning beam or scan sample, in parallel or in series-wide field, or in pixel-by-pixel sequence.

5. The computer program according to claim 1, wherein the correlation or cumulant functions are of higher order than the second order.

6. The computer program according to claim 5, wherein the acquired sequence of optical images comprises multiple sets of image stacks.

7. A computer program stored on a non-transitory medium which, when executed by a processor, performs a method of superresolution of images of objects being separated by a distance shorter than the optical diffraction limit, comprising the following steps:
   introducing observable temporal emission fluctuations in the objects of interest, the fluctuations being stochastic and independent of each other;
   generating a magnified image of a field of view encompassing the emitting objects of interest, the magnified image including pixels being substantially smaller than the point spread function introduced in magnification;
   sensing temporal fluctuations in the pixels in a succession of image frames corresponding to the temporal fluctuations in the emission of different distributed emitting objects; and
   statistically correlating the temporal fluctuations between selected pixels in the image frames; and generating a superresolved image in at least two dimensions of the emitting objects in the field of view.

8. An electronic device for analyzing a field-of-view of independently blinking objects, comprising:
hardware configured to:
calculate at least one of an autocorrelation function, an autocumulant function, a crosscorrelation function, or a crosscumulant function from temporal fluctuations of selected pixels of an x, y, t image stack to at least the second order for at least a chosen time lag or a plurality of chosen time lags
generating a superresolved and background-reduced image including pixels having an intensity value being the amplitude of the function for the at least one chosen time lag or a linear combination of amplitudes of the functions for different chosen time lags.

9. The electronic device according to claim 8, wherein said ha
select a sample or an observation image rdware device is additionally configured to: comprised of objects from the class of optically signaling objects that stochastically and independently fluctuate; and
acquire a sequence of optical images of the object as a function of time, producing the x, y, t image stack of pixels.

10. The electronic device according to claim 9, wherein the independently blinking objects could be separated by distances shorter than the diffraction limit-resolved distance of the imaging system used.

11. The electronic device according to claim 9, wherein the sample objects comprising the sample or the observation image are selected from the class comprising emitting, absorbing or scattering materials and objects labeled with such materials.

12. The electronic device according to claim 9, wherein the sequence of optical images is produced from a scanning beam or scan sample, in parallel or in series-wide field, or in pixel-by-pixel sequence.

13. The electronic device according to claim 9, wherein the correlation or cumulant functions are of higher order than the second order.

14. The electronic device according to claim 13, wherein the acquired sequence of optical images comprises multiple sets of image stacks.

15. An electronic device for performing a method of super-resolution of images of objects being separated by a distance shorter than the optical diffraction limit, comprising:
hardware configured to:
introduce observable temporal emission fluctuations in the objects of interest, the fluctuations being stochastic and independent of each other;
generate a magnified image of a field of view encompassing the emitting objects of interest, the magnified image including pixels being substantially smaller than the point spread function introduced in magnification;
sense temporal fluctuations in the pixels in a succession of image frames corresponding to the temporal fluctuations in the emission of different distributed emitting objects; and
statistically correlate the temporal fluctuations between selected pixels in the image frames
generating a superresolved image in at least two dimensions of the emitting objects in the field of view.

* * * * *